US012773518B2

(12) United States Patent
Thomas

(10) Patent No.: US 12,773,518 B2
(45) Date of Patent: Oct. 27, 2026

(54) APPARATUS AND METHOD FOR PROMPTING CONSCIOUS BREATHING

(71) Applicant: Zeeno Pty Ltd, Burleigh Heads (AU)

(72) Inventor: Damien Joseph Thomas, Burleigh Waters (AU)

(73) Assignee: ZEENO PTY LTD, Burleigh Heads (AU)

( * ) Notice: Subject to any disclaimer, the term of this patent is extended or adjusted under 35 U.S.C. 154(b) by 710 days.

(21) Appl. No.: 18/034,251

(22) PCT Filed: Nov. 1, 2021

(86) PCT No.: PCT/AU2021/051284
§ 371 (c)(1),
(2) Date: Apr. 27, 2023

(87) PCT Pub. No.: WO2022/087689
PCT Pub. Date: May 5, 2022

(65) Prior Publication Data

US 2023/0398325 A1 Dec. 14, 2023

(30) Foreign Application Priority Data

Oct. 30, 2020 (AU) ................................ 2020903943
Aug. 24, 2021 (AU) ................................ 2021106829

(51) Int. Cl.
*A61M 21/02* (2006.01)
*A61M 21/00* (2006.01)

(52) U.S. Cl.
CPC ..... *A61M 21/02* (2013.01); *A61M 2021/0022* (2013.01); *A61M 2021/0088* (2013.01); *A61M 2205/075* (2013.01); *A61M 2205/586* (2013.01)

(58) Field of Classification Search
CPC .......... A61M 21/02; A61M 2021/0022; A61M 2021/0088; A61M 16/0084;
(Continued)

(56) References Cited

U.S. PATENT DOCUMENTS 3,333,844 A 8/1967 Jurschak
5,245,991 A 9/1993 Kawaguchi
(Continued)

FOREIGN PATENT DOCUMENTS

CN 204502307 U 7/2015
CN 105579104 A 5/2016
(Continued)

OTHER PUBLICATIONS

Definition of "deflect" from Merriam-Webster Dictionary; retrieved from https://www.merriam-webster.com/dictionary/deflect.*
(Continued)

*Primary Examiner* — Joseph D. Boecker
(74) *Attorney, Agent, or Firm* — Morse, Barnes-Brown, & Pendleton, P.C.; Erin E. Bryan, Esq.

(57) ABSTRACT

The present invention relates to An apparatus for prompting conscious breathing in a subject comprising a deformable body having an internal volume, the deformable body having an opening in fluid communication with the internal volume and an external environment; and a valve located at the opening, wherein the valve is adapted to adjust a fluid flow rate between the internal volume and the external environment. The present invention assists in prompting conscious breathing.

18 Claims, 4 Drawing Sheets

(58) Field of Classification Search
CPC .......... A61M 11/008; A61M 2205/075; A61M 2205/586; A63B 23/16; A63B 23/18; A63B 23/185
See application file for complete search history.

(56) References Cited

U.S. PATENT DOCUMENTS

| | | | | |
|---|---|---|---|---|
| 5,820,523 | A * | 10/1998 | Zemer | A63B 23/16 482/49 |
| 2013/0130871 | A1 | 5/2013 | McCoy et al. | |
| 2013/0190554 | A1 | 7/2013 | Vogt et al. | |
| 2015/0148196 | A1 | 5/2015 | Hanks et al. | |
| 2016/0101252 | A1* | 4/2016 | Navarijo | A61M 16/0075 128/205.13 |
| 2017/0157348 | A1* | 6/2017 | Gillespie | A61M 16/0816 |
| 2020/0246659 | A1 | 8/2020 | Davis et al. | |
| 2021/0016034 | A1* | 1/2021 | Islava | A61M 16/0084 |

FOREIGN PATENT DOCUMENTS

| | | | |
|---|---|---|---|
| CN | 110403797 | A | 11/2019 |
| DE | 4221345 | A1 | 1/1994 |
| WO | 2020/162750 | A1 | 8/2020 |

OTHER PUBLICATIONS

Office action issued in Chinese application No. 202180074747X dated Jun. 26, 2025.
Search report issued in Chinese application No. 202180074747X dated Jun. 24, 2025.

* cited by examiner

APPARATUS AND METHOD FOR PROMPTING CONSCIOUS BREATHING

FIELD OF THE INVENTION

The present invention relates to the field of breathing. More particularly, the present invention relates to conscious breathing. Even more particularly, the present invention relates to an apparatus and method for prompting conscious breathing.

BACKGROUND TO THE INVENTION

Any reference to background art herein is not to be construed as an admission that such art constitutes common general knowledge in Australia or elsewhere.

Anxiety disorders are a common mental illness in modern society. Recent figures indicate that approximately 18% of the population in the United States of America have an anxiety disorder. A similar proportion is observed in Australia. It will be appreciated that anxiety is a significant issue.

There are a number of modalities for the treatment of anxiety. These include psychological therapy and psychotropic medication. However, it is postulated that anxiety disorders can also be alleviated by correcting breathing patterns. This is particularly the case for people who are experiencing elevated levels of anxiety or a state of panic (i.e., panic attack). It is postulated that the regulation of breathing can alleviate such problems.

The regulation of breathing is also postulated to have applications beyond the treatment of anxiety (e.g., attention deficit hyperactivity disorder). Research in children with attention deficit hyperactivity disorder suggests that repetitive movements may improve concentration and attention. This repetitive motion is referred to as stimming.

Stimming relates to self-stimulating behaviours that usually involves repetitive movement and sounds. In this regard, stimming can calm a person by blocking less predictable environmental stimuli.

Growing evidence suggests that repetitive behaviours may be incredibly useful. In this regard, stimming-type behaviours can give people, including those with autism spectrum disorder, a sense of control, assist them in coping with overwhelming external stimuli and communicate their moods. Stimming has also been identified as a useful adjunct to aid meditative practice. It is accepted that meditation is a widely used practice that promotes psychological wellbeing.

It should be appreciated that it would be advantageous to alleviate one or more of the above issues, or to at least provide the consumer with a useful or commercial alternative.

SUMMARY OF THE INVENTION

In one aspect, although it need not be the only or indeed the broadest aspect, the invention resides in an apparatus for prompting conscious breathing in a subject comprising:

- a deformable body having an internal volume, the deformable body having an opening in fluid communication with the internal volume and an external environment; and
- a valve located at the opening, wherein the valve is adapted to adjust a fluid flow rate between the internal volume and the external environment.

In an embodiment, the apparatus further comprises a fluid flow control adapted to adjust the fluid flow rate of the valve. In some embodiments, the valve and the fluid flow control are adapted to adjust the flow rate discretely or continuously. In an embodiment, the valve and the fluid flow control are adapted to adjust the fluid flow rate between at least two different flow rates. In one embodiment, the deformable body comprises a single opening. In a further embodiment, the deformably body comprises a single valve.

In one embodiment, the apparatus further comprises one or more rods extending into the internal volume. In certain embodiments, the one or more rods are connected to the handle In one embodiment, the deformable body has an internal volume of between about 50 $cm^3$ and about 150 $cm^3$, between about 50 $cm^3$ and about 100 $cm^3$, between about 100 $cm^3$ and about 150 $cm^3$, between about 75 $cm^3$ and about 125 $cm^3$, between about 76 $cm^3$ and about 105 $cm^3$, between about 90 $cm^3$ and about 110 $cm^3$, between about 100 $cm^3$ and about 110 $cm^3$, about 76 $cm^3$ or about 105 $cm^3$.

In one embodiment, the valve and the fluid flow control are configured to adjust the fluid flow rate between a low fluid flow rate, a medium fluid flow rate and a high fluid flow rate.

In an embodiment, the low fluid flow rate is between about 15 $cm^3$/sec and about 23 $cm^3$/sec, between about 17 $cm^3$/sec and about 21 $cm^3$/sec, between about 19 $cm^3$/sec and about 20 $cm^3$/sec, or about 19.1 $cm^3$/sec.

In one embodiment, the medium fluid flow rate is between about 23 $cm^3$/sec and about 33 $cm^3$/sec, between about 23 $cm^3$/sec and about 30 $cm^3$/sec, between about 25 $cm^3$/sec and about 27 $cm^3$/sec, or about 26.3 $cm^3$/sec.

In embodiments, the high fluid flow rate is between about 33 $cm^3$/sec and about 50 $cm^3$/sec, between about 35 $cm^3$/sec and about 45 $cm^3$/sec, between about 40 $cm^3$/sec and about 44 $cm^3$/sec, or about 42 $cm^3$/sec.

In one embodiment, the apparatus for prompting conscious breathing in a subject in combination with printed directions associating fluid flow rate setting of the valve to breath rate.

The invention also resides in the apparatus for use in prompting conscious breathing in a subject. The invention also resides in the apparatus when used in prompting conscious breathing in a subject. The invention also resides in an apparatus when used or for use in the treatment of anxiety. Non-limiting example of the anxiety social anxiety disorder, attention deficit hyperactivity disorder, and anxiety correlated with autism spectrum disorder. In one embodiment the conscious breathing is substantially conscious nasal breathing.

In another aspect, the invention resides in a method for prompting conscious breathing in a subject, the method including:

- the subject holding an apparatus comprising a deformable body having an internal volume, the deformable body having an opening in fluid communication with the internal volume and an external environment, and a valve located at the opening, wherein the valve is adapted to adjust a fluid flow rate therebetween;
- the subject applying pressure to the deformable body to expel fluid from the internal volume,
- the subject removing the pressure to the deformable body to allow ingress of fluid into the internal volume,
- wherein the subject inhales or exhales as fluid is expelled from the internal volume, and the other of inhale or exhale as the fluid is allowed to flow into the internal volume, to thereby prompt conscious breathing in the subject.

The apparatus and components thereof may be substantially as described hereinabove.

In an embodiment, the method may further include the step of adjusting fluid flow rate.

The various features and embodiments of the present invention referred to in the individual sections above and in the description which follows apply, as appropriate, to other sections, mutatis mutandis. Consequently, features specified in one section may be combined with features specified in other sections as appropriate.

Further features and advantages of the present invention will become apparent from the following detailed description.

BRIEF DESCRIPTION OF THE DRAWINGS

To assist in understanding the invention and to enable a person skilled in the art to put the invention into practical effect, embodiments of the invention will be described by way of example only with reference to the accompanying drawings, in which.

DETAILED DESCRIPTION OF THE INVENTION

Figure 1:
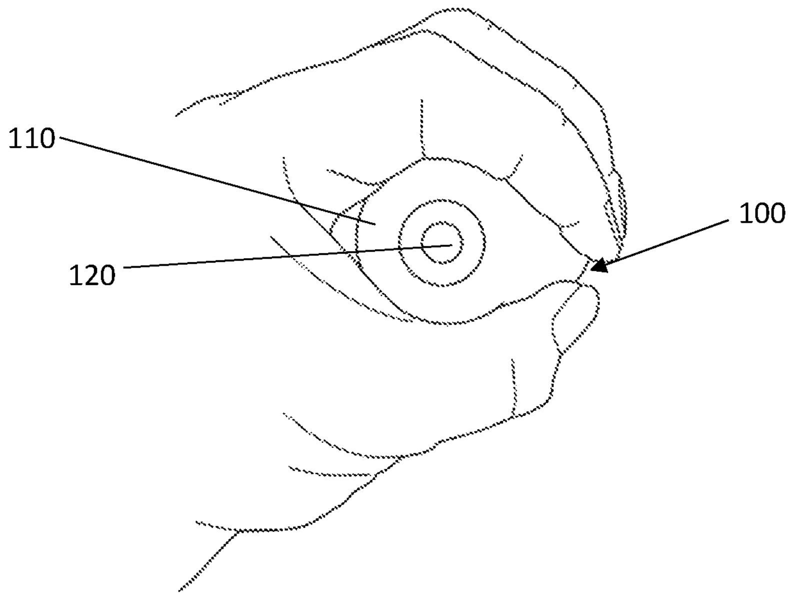
FIG. 1 is an embodiment of the apparatus for prompting conscious breathing.

Embodiments of the present invention reside primarily in an apparatus for prompting conscious breathing. Accordingly, the apparatus and method steps have been illustrated in the drawings, showing only those specific details that are necessary for understanding the embodiments of the present invention so as to not obscure the disclosure with excessive detail that will be readily apparent to those of ordinary skill in the art having the benefit of the present description.

In this specification, adjectives such as first and second, left and right, and the like may be used solely to distinguish one element or action from another element or action without necessarily requiring or implying any actual such relationship or order.

Words such as "comprises" or "includes" are intended to define a non-exclusive inclusion, such that a process, method, article, or apparatus that comprises a list of elements does not include only those elements but may include other elements not expressly listed, including elements that are inherent to such a process, method, article, or apparatus.

As used herein, the term 'about' means the amount is nominally the number following the term 'about' but the actual amount may vary from this precise number to an unimportant degree.

The present invention is predicated on the finding that the provision of an apparatus for prompting conscious breathing in a subject can alleviate some of the issues associated with anxiety disorders. Furthermore, the present apparatus provides a means of stimming to a subject, and this is advantageous in certain circumstances. In this regard, the present invention provides a subject with a prompt for conscious breathing and also facilitates stimming.

In one aspect, although it need not be the only or indeed the broadest aspect, the invention resides in an apparatus for prompting conscious breathing in a subject comprising:

- a deformable body having an internal volume, the deformable body having an opening in fluid communication with the internal volume and an external environment; and
- a valve located at the opening, wherein the valve is adapted to adjust a fluid flow rate between the internal volume and the external environment.

Figure 2:
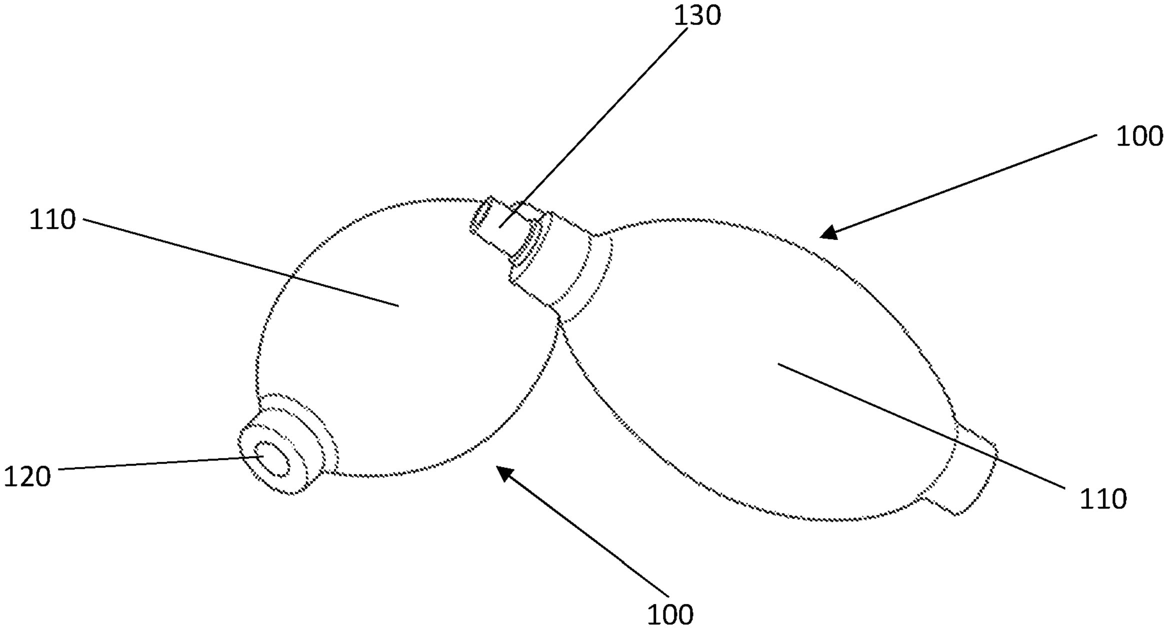
FIG. 2 shows a pair of embodiments of the apparatus for prompting conscious breathing.

Referring to FIGS. 1 and 2, there is a shown an apparatus 100 for prompting conscious breathing in a subject. The apparatus 100 comprises a body 110 having an opening 120. In this embodiment, the body 110 comprises a single opening 120. The body 110 defines an internal volume (not shown). In one embodiment, the body 110 is a deformable body. The deformable body 110 may be a hollow bulb of elastic material which can be deformed by squeezing so that the internal volume decreases and fluid (such as air for example) is expelled. Upon removing the squeezing force on the deformable body, the body regains its normal shape as fluid returns to the internal volume. The opening 120 is in fluid communication with the internal volume and the external environment. The apparatus 100 further comprises a valve 130. In this embodiment, the apparatus 100 comprises a single valve 130. The valve 130 is located at the opening 120. The valve 130 controls the fluid flow rate through the opening 120. The valve 130 is configured to adjust the fluid flow rate between at least two configurations.

It should be noted that in FIGS. 1 and 2, the apparatus is depicted to show the opening 120 (without a valve located thereon) and a valve 130 located on the opening. This is depicted to show that the opening is in fluid communication with the internal volume and the external environment.

In one embodiment, the deformable body has an internal volume of between about 50 $cm^3$ and about 150 $cm^3$, between about 50 $cm^3$ and about 100 $cm^3$, between about 100 $cm^3$ and about 150 $cm^3$, between about 75 $cm^3$ and about 125 $cm^3$, between about 76 $cm^3$ and about 105 $cm^3$, between about 90 $cm^3$ and about 110 $cm^3$, between about 100 $cm^3$ and about 110 $cm^3$, about 76 $cm^3$ or about 105 $cm^3$.

In one embodiment, the internal volume of the bulb can be adapted for an adult palm or hand, or a child palm or hand. In this regard, in general, the internal volume of the bulb for a typical adult hand is about 105 $cm^3$. For a childs hand, in general, the internal volume of the bulb is about 76 $cm^3$. It will be appreciated by the person skilled in the art that the internal volume may be in any shape. In a preferred embodiment, the internal volume has a bulb shape.

Figure 3:
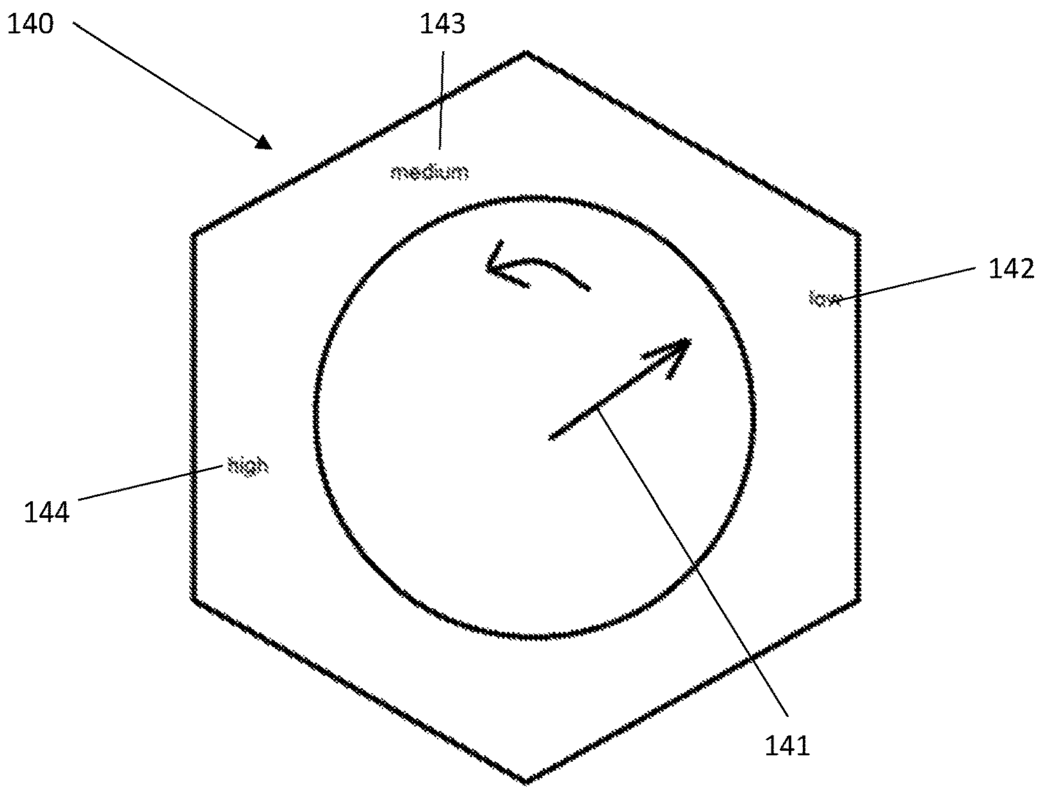
FIG. 3 shows an enlarged view of an embodiment of the fluid flow control.

The apparatus 100 may further comprise a fluid flow control 140 (an enlarged embodiment shown in FIG. 3). The fluid flow control 140 is adapted to adjust the fluid flow rate of the valve 130 between the at least two fluid flow rates. In the embodiment shown, the fluid flow control 140 is configured to adjust the fluid flow rate of the valve 130 between a low fluid flow rate, a medium fluid flow rate and a high fluid flow rate. The fluid flow control 140 may be adjusted by the subject in accordance with their requirements (mentioned in more detail hereinafter). In one embodiment, the fluid flow control 140 comprises a dial 141 which may be configured to adjust the flow rate configuration of the valve 130. In the embodiment shown in FIG. 3, the fluid flow control 140 is set at a low fluid flow 142 and can be adjusted by turning the dial 141 (in the direction of the arrow) to a medium flow rate 143 or a high flow rate 144.

In an embodiment, the low fluid flow rate is between about 15 $cm^3$/sec and about 23 $cm^3$/sec, between about 17

$cm^3$/sec and about 21 $cm^3$/sec, between about 19 $cm^3$/sec and about 20 $cm^3$/sec, or about 19.1 $cm^3$/sec.

In another embodiment, the low fluid flow rate is between about 10 $cm^3$/sec and about 16 $cm^3$/sec, between about 12 $cm^3$/sec and about 15 $cm^3$/sec, between about 14 $cm^3$/sec and about 15 $cm^3$/sec, or about 13.8 $cm^3$/sec In one embodiment, the medium fluid flow rate is between about 23 $cm^3$/sec and about 33 $cm^3$/sec, between about 23 $cm^3$/sec and about 30 $cm^3$/sec, between about 25 $cm^3$/sec and about 27 $cm^3$/sec, or about 26.3 $cm^3$/sec.

In another embodiment, the medium fluid flow rate is between about 16 $cm^3$/sec and about 25 $cm^3$/sec, between about 17 $cm^3$/sec and about 22 $cm^3$/sec, between about 18 $cm^3$/sec and about 20 $cm^3$/sec, or about 19 $cm^3$/sec In embodiments, the high fluid flow rate is between about 33 $cm^3$/sec and about 50 $cm^3$/sec, between about 35 $cm^3$/sec and about 45 $cm^3$/sec, between about 40 $cm^3$/sec and about 44 $cm^3$/sec, or about 42 $cm^3$/sec.

In another embodiments, the high fluid flow rate is between about 26 $cm^3$/sec and about 40 $cm^3$/sec, between about 28 $cm^3$/sec and about 35 $cm^3$/sec, between about 29 $cm^3$/sec and about 31 $cm^3$/sec, or about 30.4 $cm^3$/sec.

In the embodiment where the internal volume of the bulb is about 105 $cm^3$ and the low fluid flow rate is about 19.1 $cm^3$/sec, then the time required to expel the internal air volume and the time required for the ingress of air into the internal volume is about 5.5 seconds.

In the embodiment where the internal volume of the bulb is about 76 $cm^3$ and the low fluid flow rate is about 13.8 $cm^3$/sec, then the time required to expel the internal air volume and the time required for the ingress of air into the internal volume is about 5.5 seconds.

In the embodiment where the internal volume of the bulb is about 105 $cm^3$ and the medium fluid flow rate is about 26.3 $cm^3$/sec, then the time required to expel the internal air volume and the time required for the ingress of air into the internal volume is about 4 seconds.

In the embodiment where the internal volume of the bulb is about 76 $cm^3$ and the medium fluid flow rate is about 19 $cm^3$/sec, then the time required to expel the internal air volume and the time required for the ingress of air into the internal volume is about 4 seconds.

In the embodiment where the internal volume of the bulb is about 105 $cm^3$ and the high fluid flow rate is about 42 $cm^3$/sec, then the time required to expel the internal air volume and the time required for the ingress of air into the internal volume is about 2.5 seconds.

In the embodiment where the internal volume of the bulb is about 76 $cm^3$ and the high fluid flow rate is about 30.4 $cm^3$/sec, then the time required to expel the internal air volume and the time required for the ingress of air into the internal volume is about 2.5 seconds.

It will be appreciated that the fluid flow rate can be varied such that the amount of time required to expel the internal air volume and the time required for the ingress of air into the internal volume can be changed. In this regard, the time required to expel the internal air volume and the time required for the ingress of air into the internal volume at the low fluid flow rate is suitably between about 7 seconds and about 4.5 seconds, between about 6 seconds and about 7 seconds, or preferably about 5.5 seconds.

The time required to expel the internal air volume and the time required for the ingress of air into the internal volume at the medium fluid flow rate is suitably between about 4.5 seconds and about 3 seconds, between about 4.5 seconds and about 3.5 seconds, or preferably about 4 seconds.

The time required to expel the internal air volume and the time required for the ingress of air into the internal volume at the high fluid flow rate is suitably between about 3 seconds and about 2 seconds, between about 2.75 seconds and about 2.25 seconds, or preferably about 2.5 seconds.

In the embodiment shown in FIG. 3, the fluid flow control 140 comprises three different configurations: low fluid flow 142, medium fluid flow 143 and high fluid flow 144. It will be appreciated that the fluid flow control 140 may comprise two or more different configurations. In this regard, the fluid flow control 140 may comprise 2, 3, 4, 5, 6, 7, 8, 9, 10 or more configurations. It will be appreciated that the fluid flow control may be a discrete fluid flow control (as per FIG. 3) or a continuous fluid flow control (that is, the fluid flow control continuously adjusts the fluid flow of the valve as the dial is adjusted). In this regard, the flow rate of the continuous fluid flow rate can be set such that the time required for the ingress of air into the internal volume can be simply achieved.

In one embodiment, the valve is adapted to adjust between at least two discrete configurations. In another embodiment, the valve is adapted to continuously adjust fluid flow.

The valve 130 is adapted to adjust the flow rate of the fluid between the internal volume and the external environment. As such, the valve controls the amount of time required to expel the fluid from the internal volume when mechanical force is applied to the deformable body. Furthermore, when mechanical force is released, the deformable body will revert to its previous shape, this increases the volume of the internal volume and as a result fluid is drawn back into the internal volume. The person skilled in the art will appreciate that the valve 130 may be adapted to allow fluid flow therebetween at a particular rate (e.g., x $cm^3$/s) and the internal volume will have a set volume (y $cm^3$) when mechanical force is not applied. As such, the time taken to either expel fluid or allow ingress of fluid can be determined approximately by the formula: (y $cm^3$)/(x $cm^3$/s). The valve will ultimately determine the time required for the deformable body to deflate and reinflate.

As such, the flow rate can be adjusted so that the time required to deflate and inflate the deformable body (egress of fluid and ingress of fluid) can also be set as required. As the subject utilizes the deflation and reinflation of the deformable body as a conscious breathing prompt, the subject is able to adjust the parameters such that they can control the length of each prompt and thus their breathing. It will be appreciated that the length of the deflation and reinflation of the deformable body and internal volume can be altered based on the subject's requirements.

In one embodiment, the apparatus for prompting conscious breathing in a subject in combination with directions associating fluid flow rate setting of the valve to breathe rate. In a further embodiment, the directions are printed directions.

Figure 4:
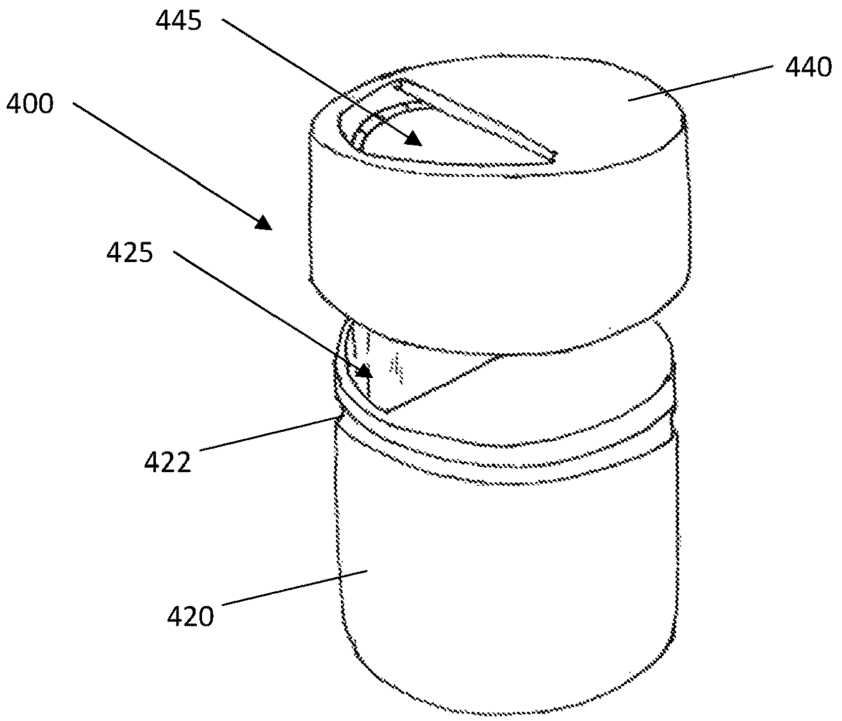
FIG. 4 shows an embodiment of a valve.

Shown in FIG. 4 is one embodiment of a valve that be utilized in the present invention. In the embodiment shown, valve 400 comprises a first body 420 and second body 440. The first body 420 comprises a first connection portion 422 that is complementary to a second connection portion (not shown). The second body 440 comprises the second connection portion. In this embodiment, the first connection portion 442 is releasably engageable with the second connection portion such that the first body 420 is rotatable relative to the second body 440. The first body 420 further comprises a first aperture 425. The second body 440 comprises a second aperture 445. In one embodiment, the first aperture 425 and the second aperture 445 have the same or similar dimensions.

In use, the first body 420 may be rotated relative to the second body 440 such that the first aperture 425 is aligned with the second aperture 445. It will be appreciated that, in this configuration, the valve 440 provides the greatest amount of fluid flow therebetween by virtue of the aligned apertures. If the user desires to reduce the fluid flow rate then the first body 420 can be rotated relative to the second body 440 such that a part of the first aperture 425 is over a part of the second aperture 445. This allows the fluid flow rate to be lowered. To facilitate ease of use, the fluid flow control may be adapted to set the fluid flow rate between the first body 420 and the second body 440. The person skilled in the art will appreciate that the above embodiment is only one example of the valve and that other valves known to the person skilled in the art may also be utilized in the present invention. In this regard, non-limiting examples of the valve include butterfly valves, ball valves, choke vales, gate valves, globe valves and knife valves.

In one embodiment, the deformable body is in the form of a bulb. In one embodiment, the deformable body is formed of a material that can be deformable under mechanical force. In one embodiment, the mechanical force is applied by a hand of the subject. In one embodiment, the deformable body is formed of a plastic or polymer.

As the deformable body is deformed by mechanical force, the fluid within the internal volume is displaced and expelled to the external environment. The valve 130 controls the rate in which the fluid is expelled from the internal volume through the opening 120 and, subsequently, the rate of ingress of the fluid into the internal volume when mechanical force is removed.

This allows the present invention to be utilized as a prompt for exhaling and inhaling. In this regard, the subject may either exhale or inhale whilst mechanical force (pressure applied by hand) is applied to the deformable body (and fluid is flowing out of the internal volume). Subsequently, the subject may exhale or inhale (the other of the above) whilst mechanical force is no longer applied (and fluid is flowing back into the internal volume). It will be appreciated that this acts as a prompt for the person to inhale and exhale at the desired rate. This allows the subject to consciously control their breathing and address some of the issues mentioned hereinabove.

The use of the present apparatus also facilitates repetitive movement (stimming) and, as mentioned above, these repetitive movements may improve concentration, attention, and decision making. In this regard, the subject may apply mechanical pressure onto the deformable body at consistent intervals. This stimming-type behaviour can give people, including those with autism a sense of control, helping them cope with overwhelming external stimuli and be a way to calm and communicate their moods.

Figure 5:
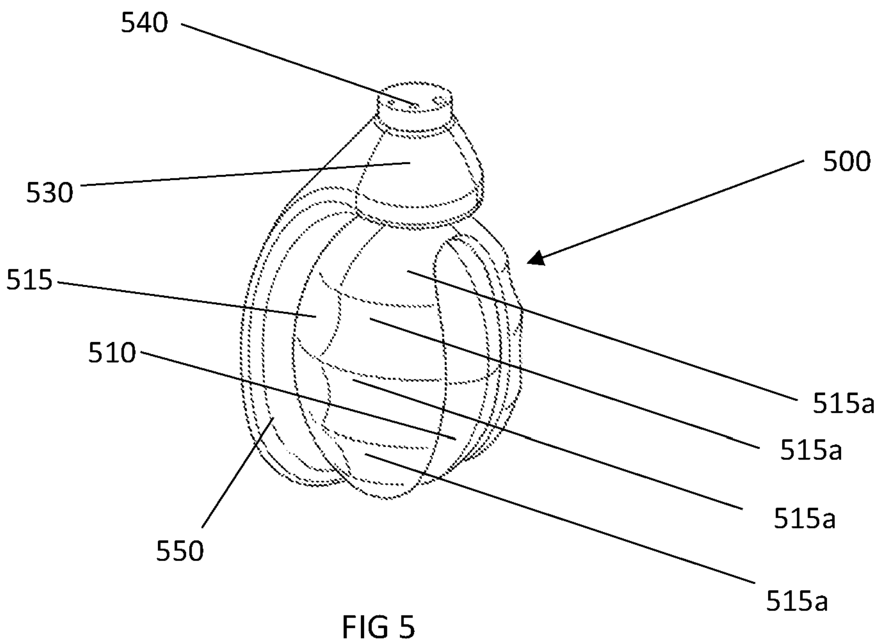
FIG. 5 shows another embodiment of the apparatus for prompting conscious breathing.

FIG. 5 shows another embodiment of an apparatus 500 for prompting conscious breathing in a subject. The apparatus 500 comprises a body 510 having an opening (not shown). In the embodiment shown, the body 510 comprises a single opening. The body 510 defines an internal volume (not shown). In one embodiment, the body 510 is a deformable body. The deformable body 510 may be a hollow bulb of elastic material which can be deformed by squeezing so that the internal volume decreases and fluid (such as air for example) is expelled. Upon removing the squeezing force on the deformable body, the body 510 regains its normal shape as fluid returns to the internal volume. The opening is in fluid communication with the internal volume and the external environment. The apparatus 500 further comprises a valve 530. In the embodiment shown, the apparatus 500 comprises a single valve. The valve 530 is located at the opening. The valve 530 controls the fluid flow rate through the opening. In the embodiment shown, the apparatus 500 further comprises fluid flow control 540. The fluid flow control 540 is configured to adjust the fluid flow rate of the valve between at least two configurations. In the embodiment shown, the fluid flow control 540 is configured to adjust the fluid flow rate of the valve 530 between three configurations. In the embodiment shown, the body comprises a cover 515 comprises grooves **515*a* which facilitate grasping of the body 510** by a hand. This provides an ergonomically design for the user. In one embodiment, the grooves may be formed on an outer surface of the body.

Studies suggest that human affiliative touch leads to a general increase in parasympathetic nervous system activity. Neurochemically, this reduction in arousal in response to cutaneous stimulation is hypothesised to be mediated by the release of oxytocin. Recent neuroscientific studies of human skin nerves has led to the identification and characterisation of a class of touch sensitive nerve fibres named C-tactile afferents. Neither itch nor pain receptive, these unmyelinated, low threshold mechanoreceptors, found only in hairy skin, respond optimally to low force/velocity stroking touch. Notably, the speed of stroking which C-tactile afferents fire most strongly (3 cm/s) to is also that which people perceive to be most pleasant. It is postulated that stroking of C-tactile afferents produces an anxiolytic response within the human body. Further studies have also identified that muscle afferent feedback provides critical information pertaining to cardiorespiratory responses. Recent advances in the field have identified the interconnectedness of chemoreceptor and extra-chemoreceptor mechanisms associated with ventilation control.

In the embodiment shown in FIG. 5, the apparatus 500 further comprises a handle or strap 550. In use, the handle or strap 550 suitably rests on, or close to, the back of a hand of the subject. In this regard upon application of a squeezing force on the deformable body, air is expelled through the handle or strap 550. This results in movement in the handle 550 and results in a stroking sensation on the back of the hand. This is postulated to stimulate the c-tactile afferents.

In one embodiment, the handle or strap 550 defines an internal volume. The internal volume of the handle 550 may be in fluid communication with the internal volume of the body 510. That is, the internal volume of the handle is in fluid communication with the valve 530, which in turn is in fluid communication with the internal volume of the body 510. It should be appreciated that the only substantial point in which the fluid in the internal volume of the body 510 can be expelled is through the an open-end at a distal end of the handle 550. In one embodiment regard, the distal end of the handle or strap 550 comprises an aperture (not shown). The aperture facilitates fluid flow from the internal volume of the body 510 and handle 550 with the external environment. In one embodiment, the handle 550 is connected to the valve 530. In another embodiment, the handle 550 is integrally formed with the valve 530. In yet another embodiment.

It will be appreciated the present invention provides a prompt for conscious breathing and facilitates stimming. As such, the present apparatus is capable of providing multiple modalities to addressing the above problems. It is postulated that conscious breathing and stimming together form an effective treatment to alleviate stress and anxiety.

Figure 6:
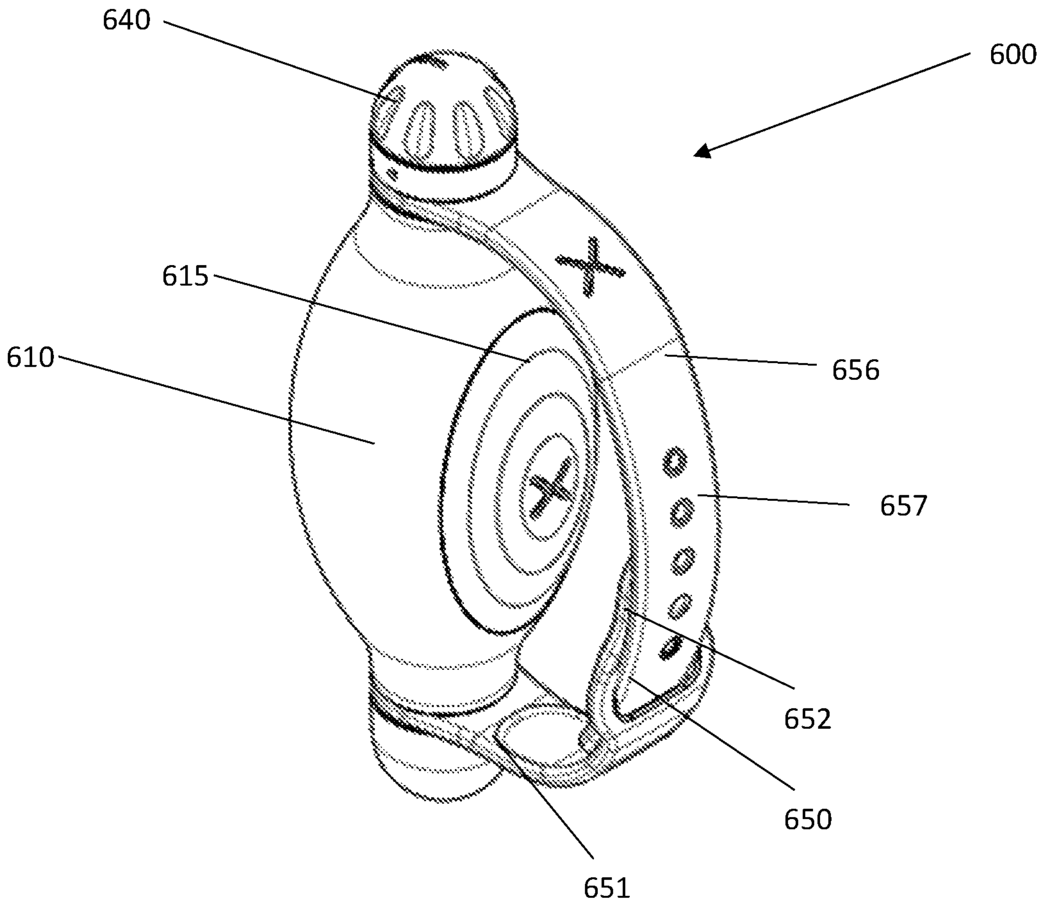
FIG. 6 shows another embodiment of the apparatus for prompting conscious breathing.

In the embodiment shown in FIG. 6, the apparatus 600 further comprises a handle or strap 650. In use, the handle or strap 650 suitably rests on the back of a hand of the subject.

In one embodiment, the handle or strap 650 is replicable. In this regard, the handle or strap may comprise a first handle member 651 removably attachable to an end of body 610. In this embodiment, the handle does not define an internal volume in communication with the internal volume of the body. The distal end of the first handle member 651 is provided with a first adjustable attachment region 652. The handle or strap may further comprise a second handle member 656 removably attachable to another end of body 610. The distal end of the second handle member 656 is provided with a second adjustable attachment region 657 that is complementary to the first adjustable attachment region 652. In one embodiment, the first adjustable attachment region 652 and the second adjustable attachment region 657 are a belt and buckle arrangement. The person skilled in the art will appreciate that a number of complementary attachment portions may be utilized with the claimed invention. In the embodiment shown, the apparatus 600 further comprises fluid flow control 640.

In an embodiment, the apparatus 600 may further comprise a palm pad 615. The palm pad 615 is removably attachable to the body 610. The palm pad 615 can suitably be removed for hygiene purposes, or to provide a different tactile feel.

Research suggests that neurons respond in a highly idiosyncratic manner to different aspects of texture. In this regard, some neurons respond to coarse features of a texture whilst others may respond to smooth surfaces. It is postulated that specific textures will evoke certain affective responses. The apparatus advantageously provides an interchangeable palm pad which can be changed to different textures to evoke certain affective responses. In one embodiment, the palm pad comprises a soft skin-like surface.

Figure 7:
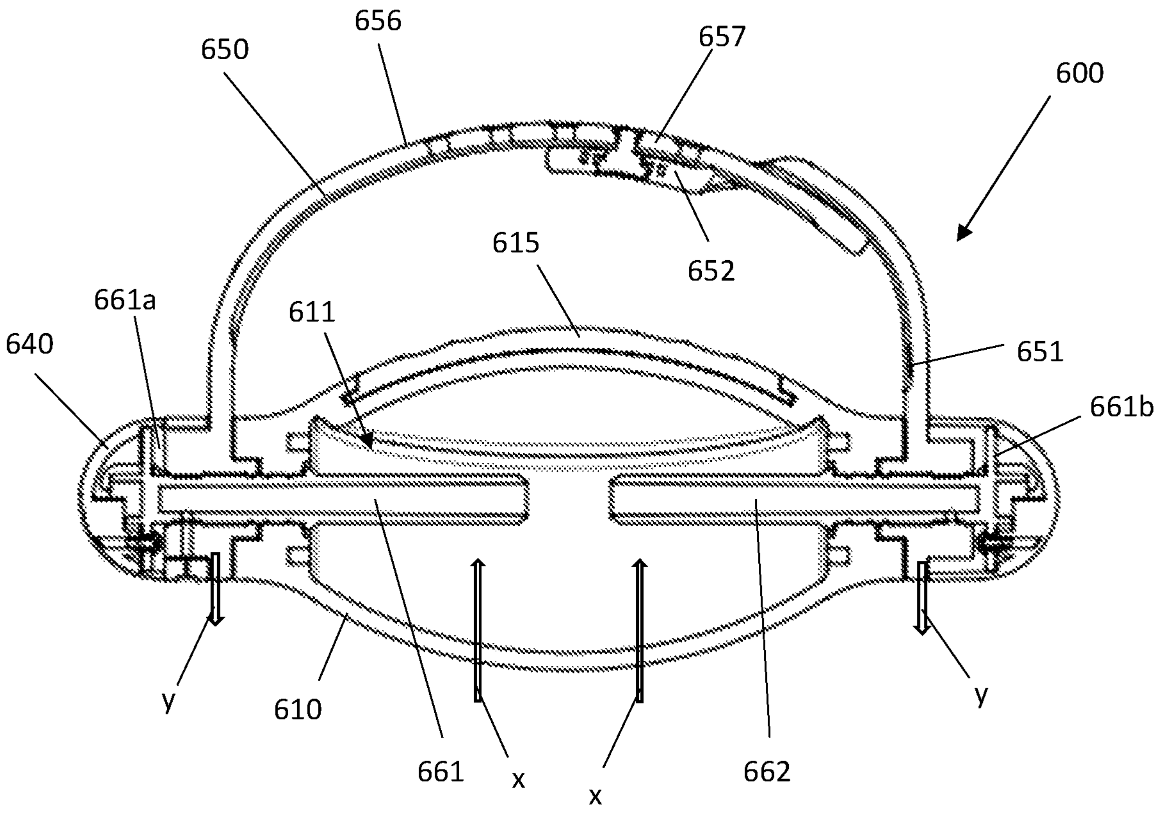
FIG. 7 shows a cross sectional view of the embodiment shown in FIG. 6.

Shown in FIG. 7 is a cross section of the apparatus 600 shown in FIG. 6. As shown, the apparatus 600 comprises internal volume 611 defined by body 610. In one embodiment, the apparatus 600 further comprises one or more elongate members. The elongate rods are configured to respond to the body being depressed. In this regard, the elongate rods may move in response to the body being depressed, and subsequently move back to their original position when the body is returning to its original shape. In an embodiment, the elongate members are rods. In this regard, the apparatus 600 may further comprise one or more rods extending into the internal volume 611. In the embodiment shown, the apparatus 600 comprises two rods 661, 662. The rods 661, 662 are suitably connected to the handle or strap 650. The body 610 is also adapted to receive ends of the handle or strap 650. In the embodiment shown, the rods 661, 662 comprise anchor portions 661*a*, 662*a* which extend away from the rods 661, 662, respectively. The anchor portions 661*a*, 662*a* secures the rods 661, 662. As shown, the rods extend through the body 610 and forms a seal therewith. The rods 661, 662 may suitably comprise a flange that assists in forming a seal with the body 610.

The rods enable the handle or strap 650 to provide a stimuli. In one embodiment, the stimuli is a 'patting motion'. The inventors believe that the patting motion stroke or 'fire' the C-tactile afferents producing an anxiolytic response. In this regard, as the subject compresses the bulb, the action pushes down on the rods (shown by the arrows labelled x) and this in turn pushes the ends of the rods out (shown by the arrows labelled y) which inturn pulls the strap onto the back of the hand. This stimulates a patting action.

In one embodiment, the handle or strap 650 may comprise a surface to provide a particular tactile feel. In this regard, the handle of strap 650 may be interchangeable for another handle or strap having a different surface with a different tactile feel. It will be appreciated that this in combination with the changeable palm pad allows for a patting motion with different tactile stimuli.

Typical solutions to prompting conscious breathing usually involve interfacing with the mouth of the subject. In this regard, an object or assembly may be placed over the mouth of the subject to control breathing. The present invention does not require such an interface with the subject. The present invention provides a prompt for the subject to breath consciously in an unobtrusive manner. Furthermore, the present invention can be configured to avoid deep breathing. In one embodiment, the present apparatus is not required to be in physical contact with the mouth of the subject. In one embodiment, the present invention is not utilized in promoting deep breathing.

The present apparatus represents a multimodal approach to alleviate stress and anxiety through conscious breathing and tactile somatosensory input. The present apparatus is postuled to provide significant enhancement on current techniques aimed at achieving similar outcomes. Current therapeutic modalities, such as Eye Movement Desensitization and Reprocessing (EMDR), utilize tactile interface (tapping), thus incorporating somatosensory input. The present apparatus offers an alternative method of achieving tactile somatosensory arousal. The current apparatus also effectively combines the practice of conscious breathing with somatosensory input.

It is widely considered there remains a preferred system of breathing; that is, nasal breathing with an approximate respiratory rate of 6-10 breaths per minute is considered optimal for adult humans. However, many children and adults have developed suboptimal breathing processes that are adversely impacting everyday functioning, including within the context of allergies, anxiety, and capacity to manage everyday stressors.

The majority of children and adults living in the western world are habitually over-breathing or breathing through the mouth (i.e., mouth breathing). In children, mouth breathing can lead to physical abnormalities and cognitive challenges. Children who are not treated for mouth breathing can develop:

long, narrow faces;
narrow mouths;
gummy smile;
dental malocclusion, including a large overbite and crowded teeth;
poor posture; and/or
sleep disorders.

Typically, the present solutions for correcting dysfunctional breathing involves the use of oral interface devices. Such intervention requires 'mouth breathing'. It is postulated that such intervention may, in fact, ultimately contribute to further breathing dysfunction. The present device allows for the practice of preferred respiratory process through the tactile modality, hence alleviating the requirement for mouth breathing.

Breathing too deeply, too often, or too quickly can lead to hyperventilation. Hyperventilation is commonly defined as rapid or deep breathing that is often caused by anxiety and/or stress. Over-breathing is known to disturb breathing biochemistry. In this instance, the term biochemistry refers to the relative concentrations of oxygen and carbon dioxide in the blood. When a subject breathes in too large a volume of air, the subject must also breathe out an equivalent amount of air. This action lowers the level of carbon dioxide in the blood. Carbon dioxide ($CO_2$) is essential because it stimulates the process by which oxygen is released from circulating blood cells into the body to be used. The exaggerated loss of $CO_2$, during prolonged deep breathing, results in adverse physiological and psychological outcomes. The present apparatus address these issues by prompting conscious breathing, which involves nasal breathing rather than mouth breathing. Furthermore, the present apparatus prompts the subject for nasal breathing at the desired interval.

In another form, the invention resides in a method for prompting conscious breathing in a subject, the method including:

- providing an apparatus comprising a deformable body having an internal volume, the deformable body having an opening in fluid communication with the internal volume and an external environment, and a valve located at the opening, wherein the valve is adapted to adjust a fluid flow rate therebetween;
- applying pressure to the deformable body to expel fluid from the internal volume,
- removing the pressure to the deformable body to allow ingress of fluid into the internal volume,
- wherein the subject inhales or exhales as fluid is expelled from the internal volume, and the other of inhale or exhale as the fluid is allowed to flow into the internal volume,
- to thereby prompt conscious breathing in the subject.

The apparatus of components thereof may be substantially as described hereinabove.

The method may further include the step of adjusting fluid flow rate.

The above description of various embodiments of the present invention is provided for purposes of description to one of ordinary skill in the related art. It is not intended to be exhaustive or to limit the invention to a single disclosed embodiment. As mentioned above, numerous alternatives and variations to the present invention will be apparent to those skilled in the art of the above teaching. Accordingly, while some alternative embodiments have been discussed specifically, other embodiments will be apparent or relatively easily developed by those of ordinary skill in the art. Accordingly, this invention is intended to embrace all alternatives, modifications and variations of the present invention that have been discussed herein, and other embodiments that fall within the spirit and scope of the above described invention.

What is claimed is:

1. An apparatus for prompting conscious breathing in a subject comprising:

- a deformable body having an internal volume, the deformable body having an opening in fluid communication with the internal volume and an external environment;
- two rods connected to the deformable body and extending into the internal volume, the two rods adapted to deflect in response to deformation of the deformable body;
- a strap connected to the two rods, the deformation of the deformable body causes the strap to provide a stimuli to the subject; and
- a valve located at the opening, wherein the valve is adapted to adjust a fluid flow rate between the internal volume and the external environment.

2. The apparatus of claim 1, wherein the apparatus further comprises a fluid flow control adapted to adjust the fluid flow rate of the valve.

3. The apparatus of claim 2, wherein the valve and the fluid flow control are adapted to adjust the flow rate discretely or continuously.

4. The apparatus of claim 2, wherein the valve and fluid flow control are adapted to adjust the fluid flow rate between at least two different flow rates.

5. The apparatus of claim 3, wherein the valve and fluid flow control are configured to adjust the fluid flow rate between a low fluid flow rate, a medium fluid flow rate and a high fluid flow rate.

6. The apparatus of claim 5, wherein the low fluid flow rate is between about 13.8 $cm^3$/see and about 19.1 $cm^3$/see, wherein the medium fluid flow rate is between about 19 $cm^3$/see and about 26.3 $cm^3$/see, and wherein the high fluid flow rate is between 30.4 $cm^3$/see and about 42 $cm^3$/sec.

7. The apparatus of claim 5, wherein the time required to expel the internal volume and the time required for an ingress of air into the internal volume is 5.5 seconds when configured to the low fluid flow rate, is 4 seconds when configured to the medium fluid flow rate, and is 2.4 seconds when configured in the high fluid flow rate.

8. The apparatus of claim 1, wherein the internal volume of the strap is in fluid communication with the valve and internal volume of the deformable body.

9. The apparatus of claim 1, wherein the strap comprises an aperture at a distal end thereof.

10. The apparatus of claim 1, wherein the strap is integrally formed with the valve.

11. The apparatus of claim 1 for use prompting conscious breathing in the subject.

12. The apparatus of claim 1, wherein the strap is interchangeable.

13. The apparatus of claim 12, wherein the two rods are connected to the strap.

14. The apparatus of claim 1, wherein the strap is adjustable.

15. The apparatus of claim 1, wherein the deformable body has an internal volume of between about 76 $cm^3$ and about 105 $cm^3$.

16. The apparatus of claim 1, wherein the deformable body comprises a single opening and/or a single valve.

17. The apparatus of claim 1, wherein the stimuli is a patting motion.

18. A method for prompting conscious breathing in a subject, the method including:

- the subject holding an apparatus comprising a deformable body having an internal volume, the deformable body having an opening in fluid communication with the internal volume and an external environment, two rods connected to the deformable body and extending into the internal volume, the two adapted to deflect in response to deformation of the deformable body; a strap connected to the two rods, the deformation of the deformable body causes the strap to provide a stimuli to the subject; and a valve located at the opening, wherein the valve is adapted to adjust a fluid flow rate between the internal volume and the external environment;
- the subject applying pressure to the deformable body to expel fluid from the internal volume,
- the subject removing the pressure to the deformable body to allow ingress of fluid into the internal volume.

* * * * *